Figure 1:
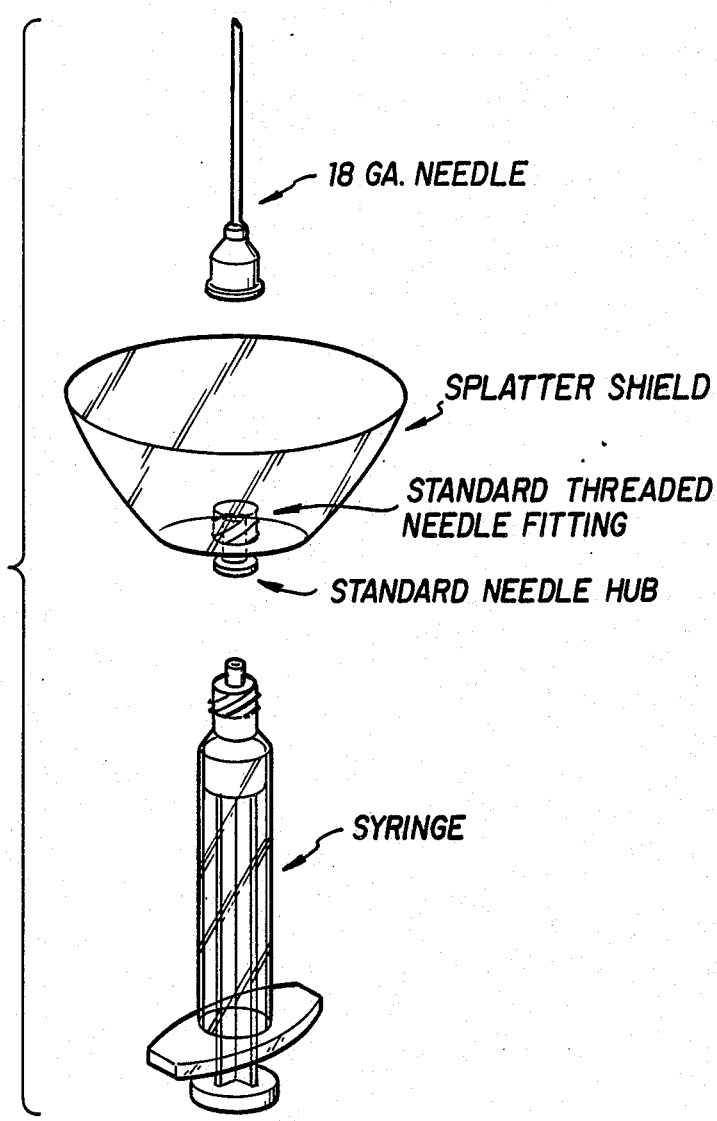
Figure 2A:
Figure 2B:
Figure 2C:
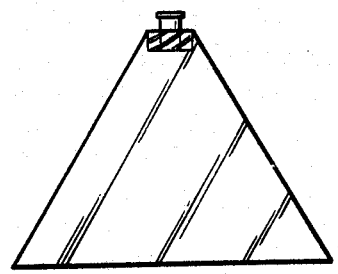
Figure 2D:
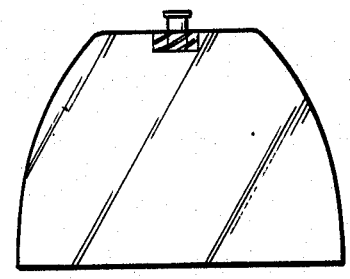
Figure 2E:
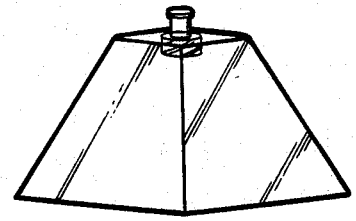

United States Patent [19]

Roberts

[11] Patent Number: 4,898,588
[45] Date of Patent: Feb. 6, 1990

[54] HYPODERMIC SYRINGE SPLATTER SHIELD

[76] Inventor: Christopher W. Roberts, P.O. Box 445, Derby Line, Vt. 05830

[21] Appl. No.: 258,790

[22] Filed: Oct. 17, 1988

[51] Int. Cl.$^4$ ................................................ A61M 5/00
[52] U.S. Cl. ..................................... 604/187; 604/242
[58] Field of Search ............... 604/187, 192, 198, 263, 604/39, 115, 117, 242, 241, 240

[56] References Cited

U.S. PATENT DOCUMENTS

| | | | |
|---|---|---|---|
| 1,934,046 | 11/1933 | Demarchi | 604/115 |
| 2,845,065 | 7/1958 | Gabriel | 604/242 X |
| 4,232,669 | 11/1980 | Nitshke | 604/263 |
| 4,769,003 | 9/1988 | Stamler | 604/39 |

Primary Examiner—John D. Yasko
Attorney, Agent, or Firm—Edward McC. Roberts

[57] ABSTRACT

A splatter shield for use with a hypodermic syringe to prevent high-angle back-splatter, from syringe lavage, into the user's face. The splatter shield comprises a preferably circular sheet of stiff material which is preferably colorless and transparent, having a central tube which is attached thereto and which passes through the center of said sheet and projects on at least one side of said sheet sufficiently to have one end adapted to receive a standard syringe fitting and the other end adapted to receive a standard hypodermic needle. Said generally circular sheet is preferably cupped about the central tube so as to be concave on the side of the guard which has the needle-receiving, central tube end. The radius of the generally circular sheet and the degree of cupping in the preferred embodiment are chosen so that the shield flares out from the needle, like a skirt, sufficiently to intercept lavage-splatter at about 60° to 90° from the plane of the wound, and also chosen such that the point of the needle, in use, projects beyond the plane of the splatter shield or the base thereof.

6 Claims, 2 Drawing Sheets

HYPODERMIC SYRINGE SPLATTER SHIELD

This invention relates to a splatter shield for use with a hypodermic syringe, and more specifically to a splatter shield having means adapted to lessen the likelihood that the user will accidentally suffer contamination of the eyes, nose and mouth from back-splatter during wound lavage with a hypodermic syringe.

Modern medical techniques have resulted in the extensive use of hypodermic syringes to lavage wounds. One of the problems which has occurred as a result of frequent use of the existing products has been undesired back-splatter of bloody and possibly infectuous washings, with contamination suffered by persons employing hypodermic syringes for lavage. Such inadvertent contamination of the lavager's eyes, nose and mouth with splattered lavage material has necessitated treatment of diseases that result from the contamination. Such accidental contamination and illnesses are troublesome not only in a physical sense, but also financially as a result of the ultimate cost in terms of lost employee time, the cost of treating the contaminated user and the associated recordkeeping. This is in addition to the anguish and worry that may be experienced by the contaminated worker.

Today, the blood-transmitted diseases of primary concern to health practitioners are hepatitis B and AIDS. These are of particular concern during wound lavage because this procedure is often carried out under emergency conditions, before any blood tests have been carried out on the patient. Insofar as possible the health practitioner must therefore carry out the lavage so as to avoid contamination of his or her eyes, nose and mouth with blood that may be infective.

There is therefore a need for a splatter shield to protect the lavager of wounds from back splatter of bloody washings from the lavage procedure. Inasmuch as the lavager's face is generally directly in line with the wound and the syringe, low-angle back-splatter is of little concern. It is the high-angle splatter that the lavager's face needs to be shielded from.

This invention provides a splatter shield for use with a hypodermic syringe to prevent high-angle back-splatter from syringe lavage into the user's face. The splatter shield comprises a sheet of stiff material which is preferably circular, colorless and transparent, having a central tube which is attached thereto and which passes through the center of said sheet and projects on at least one side of said sheet sufficiently to have one end adapted to receive a standard syringe fitting and the other end adapted to receive a standard hypodermic needle. Said preferably circular sheet is preferably cupped about the central tube so as to be concave on the side of the shield which has the needle-receiving, central tube end. The dimensions of the sheet and the degree of cupping in the preferred embodiment are chosen so that the shield flares out from the needle, like a skirt, sufficiently to intercept lavage splatter at about 60° to 90° from the plane of the wound, and also chosen such that the point of the needle, in use, projects beyond the plane of the splatter shield or the base thereof.

From U.S. Pat. No. 4,769,003, issued Sept. 6, 1988 on application of Keith Stamler, it is known to use a bell-shaped splashback shield which is large enough to completely isolate and contain the entire length of the lavage needle, the wound area being lavaged, and the entire lavage liquid including the washed-off blood and detritus. This necessarily makes the practitioner's visibility of wound and action area dependent on the drainage of the wash liquid down the sides of the splashback shield.

The shield of this invention leaves the practitioner a clear view of the wound and the action area because the shield of this invention is small enough to allow the lavage needle to extend well below the shield. As indicated above in the discussion of the objects of this invention, it is only the high-angle lavage splattering that is of concern to the practitioner. The splatter guard of this invention, with the needle projecting below the base plane of the guard, does not contact the low-angle lavage splatters, only the relatively rare high-angle splatters that are of concern to the practitioner who wishes to avoid facial contamination. As a result the shield does not readily get splattered and hard to see through. Furthermore the practitioner can readily look around the splatter shield of this invention, the shield needing to be held directly between the practitioner's face and the wound only at the moment of wash-liquid expression from the needle tip. As a result the inventive shield is easy to use and is not intrusive in the lavage process.

Furthermore, the shield of this invention allows most of the expressed wash-liquid from the lavage procedure to drain away from the wound area for the purposes of clean-up and preparation of a sterile area for treatment of the wound by surgical or other procedure. One advantage of the shield of this invention is that it does not in any way interfere with the usual lavage procedure and sterile work-up procedure with which the physician is familiar.

FIG. 1 depicts the splatter shield in a preferred embodiment as a frustum of a cone with standard syringe fittings on the central tube. Shown in FIG. 1 is the familiar and preferred Luer Lok fittings. In FIG. 1 a needle and syringe (neither of which is part of this invention) are shown in an exploded view, positioned for attachment and use.

FIG. 2 shows some other optional shapes (FIGS. 2a–2e) for the splatter shield. In general, the angle whose rotation describes the substantially conical shield should be in the range of about 60° to 180°. At 180° the shield is flat (FIG. 2a). At 60° the shield is approaching the operative limit where further diminution of the angle would lead to ineffective shielding with too-narrow a shielded field. The preferred angle for rotation to describe the preferred cone is about 90°.

As can be appreciated the height of the cone will be determined in part by the length of the needle to be used therewith. The height of the cone should not project the base of the cone beyond the open end of the needle when the needle is attached and ready for use. Preferably the needle in use projects beyond the base of the cone to the extent of about 10% to 50% of the needle's length. By "base of the cone" is meant the broad, open end of the cone. As will also be appreciated from the Figures, the splatter shield need not be a true conic section, but can be seen to be generally conical in shape. A hemisphere or hemisphere section is also a useful shield shape.

The material from which the splatter shield of this invention is made can be any reasonably stiff material that can be shaped as needed. Particularly useful are polymer materials such as transparent thermoplastics. Polyesters, acrylics, and polystyrene are exemplary of useful materials. Polycarbonate is the preferred material for manufacturing the splatter shield. Although the splatter shield is designed to not contact the patient, and in use the shield would ordinarily not contact the patient, it would be preferable to package the shield in sterile condition so it would not pose a problem for the practitioner.

What I claim is:

1. A splatter shield for use with a hypodermic syringe during wound lavage, comprising a sheet of stiff material and a central tube which is attached to the sheet as it passes through the center thereof, said tube projecting on at least one side of said sheet and having one end adapted to receive a standard syringe fitting and the other end adapted to receive a standard hypodermic needle, wherein the shape of the sheet is a cone or a conic frustum of about 60° to 180° with the concavity of the cone being on the side of the sheet having the needle-receiving central tube end, and wherein the size and degree of concavity of the sheet is such as to allow the hypodermic needle, in use, to project below the base of the cone to the extent of about 10% to about 50% of the needle's length.

2. The splatter shield of claim 1 wherein the sheet when flattened out is substantially circular.

3. The splatter shield of claim 1 wherein the sheet is substantially colorless and transparent.

4. The splatter shield of claim 1 wherein the shape of the sheet is a cone or conic frustum of about 90°.

5. The splatter shield of claim 1 wherein the central tube ends are adapted to receive the needle and the syringe for threaded attachment.

6. The splatter shield of claim 3 wherein the shield is made of a sterilizable thermoplastic polymeric solid material.

* * * * *